United States Patent
Pivonka et al.

(10) Patent No.: US 10,320,232 B2
(45) Date of Patent: Jun. 11, 2019

(54) METHOD OF MAKING AND USING AN APPARATUS FOR A LOCOMOTIVE MICRO-IMPLANT USING ACTIVE ELECTROMAGNETIC PROPULSION

(71) Applicant: The Board of Trustees of the Leland Stanford Junior University, Palo Alto, CA (US)

(72) Inventors: Daniel Michael Pivonka, Palo Alto, CA (US); Anatoly Anatolievich Yakovlev, Mountain View, CA (US); Ada Shuk Yan Poon, Redwood City, CA (US); Teresa H. Meng, Saratoga, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 281 days.

(21) Appl. No.: 15/217,827

(22) Filed: Jul. 22, 2016

(65) Prior Publication Data
US 2017/0054332 A1 Feb. 23, 2017

Related U.S. Application Data

(63) Continuation of application No. 13/591,188, filed on Aug. 21, 2012, now Pat. No. 9,433,750, which is a (Continued)

(51) Int. Cl.
| | | |
|---|---|---|
| H02J 7/02 | (2016.01) |
| H02J 7/34 | (2006.01) |
| H02J 50/10 | (2016.01) |
| H02J 50/80 | (2016.01) |
| H02J 50/90 | (2016.01) |
| A61B 1/00 | (2006.01) |
| A61B 5/07 | (2006.01) |
| A61M 25/01 | (2006.01) |
| A61M 31/00 | (2006.01) |
| H02J 50/23 | (2016.01) |
| H02J 50/27 | (2016.01) |

(52) U.S. Cl.
CPC .......... *H02J 50/10* (2016.02); *A61B 1/00158* (2013.01); *A61B 5/07* (2013.01); *A61M 25/0116* (2013.01); *A61M 25/0127* (2013.01); *A61M 31/002* (2013.01); *H02J 7/025* (2013.01); *H02J 50/23* (2016.02); *H02J 50/27* (2016.02); *H02J 50/80* (2016.02); *H02J 50/90* (2016.02); *H02J 7/345* (2013.01)

(58) Field of Classification Search
CPC .. H02J 7/025; H02J 7/345; H02J 50/10; H02J 50/23; H02J 50/27; H02J 50/80; H02J 50/90; A61B 1/00158; A61B 5/07; A61M 25/0116; A61M 25/0127; A61M 31/002
USPC .......................................... 307/104
See application file for complete search history.

(56) References Cited

U.S. PATENT DOCUMENTS

| | | | |
|---|---|---|---|
| 8,504,138 B1 * | 8/2013 | Pivonka ................ | A61B 1/041 600/407 |
| 8,634,928 B1 * | 1/2014 | O'Driscoll ......... | A61N 1/37229 607/33 |
| 9,433,750 B2 * | 9/2016 | Pivonka ............. | A61M 25/0116 |

* cited by examiner

*Primary Examiner* — Hal Kaplan
(74) *Attorney, Agent, or Firm* — Pillsbury Winthrop shaw Pittman LLP

(57) ABSTRACT

Described is a locomotive implant for usage within a predetermined magnetic field. In one embodiment magnetohydrodynamics is used to generate thrust with a plurality of electrodes. In another embodiment, asymmetric drag forces are used to generate thrust.

24 Claims, 19 Drawing Sheets

Related U.S. Application Data continuation-in-part of application No. 12/485,654, filed on Jun. 16, 2009, now Pat. No. 8,504,138, which is a continuation-in-part of application No. 12/485,641, filed on Jun. 16, 2009, now Pat. No. 8,634,928.

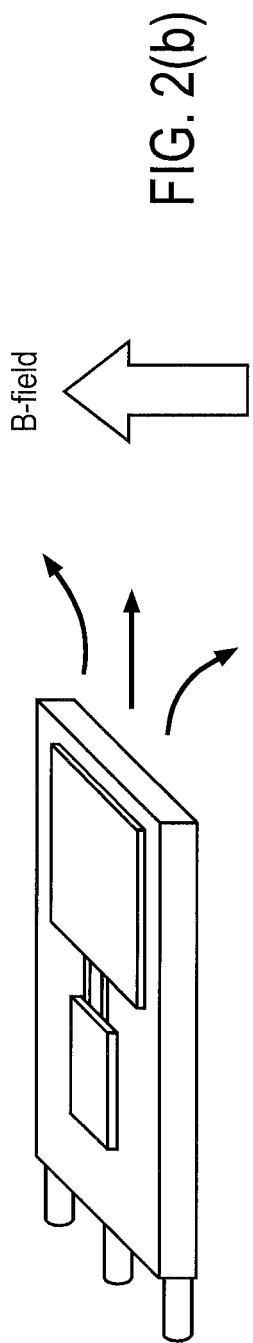
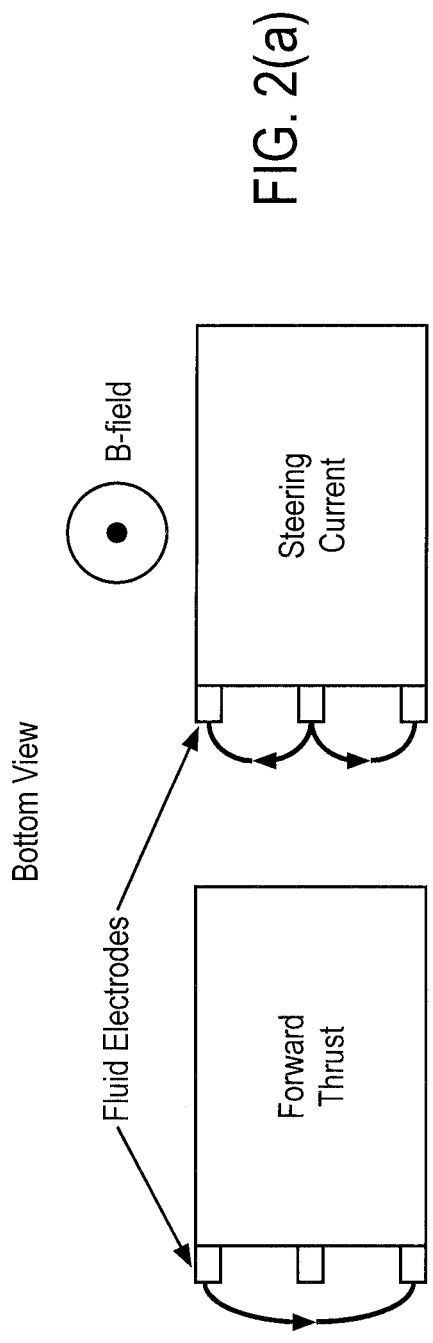

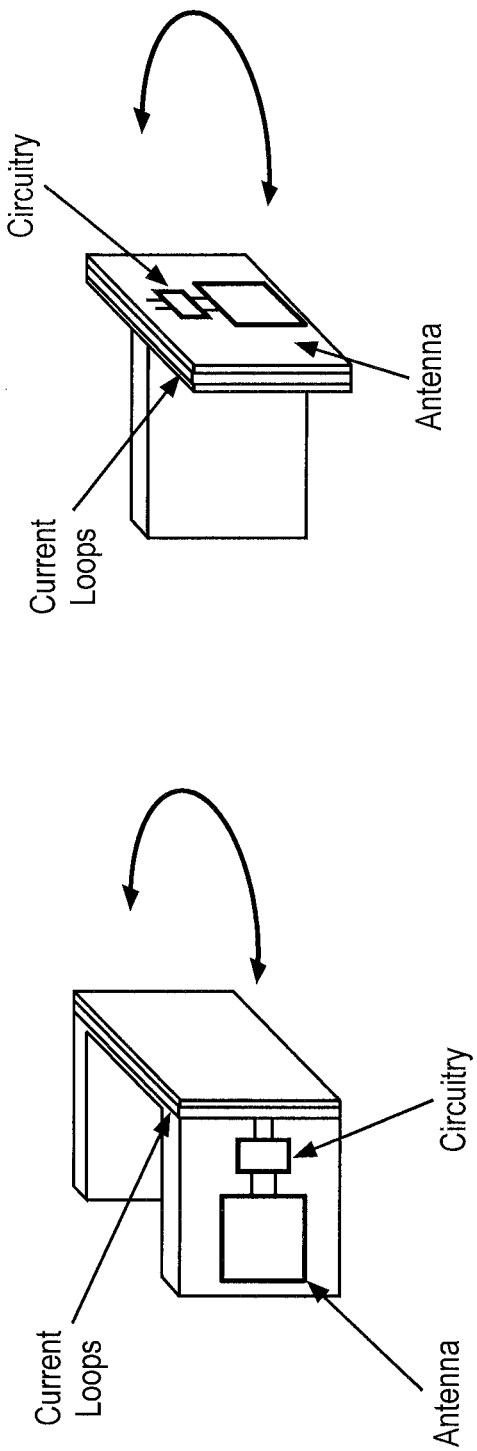

$V_{rf}(t)=V_{rf+}-V_{rf-} = A[1+k_a m(t)]\cos(w_c t)$   Modulation Depth = $|k_a m(t)| \leq 1.0$

= "0"    = "1"

m(t)

Vrf(t)

$V_{env}$ ···
$V_{ref}$ —

$\underline{AV_{dd}/2}$ —
$\underline{AV_{integ}}$ ···

Clk ···
Data —

METHOD OF MAKING AND USING AN APPARATUS FOR A LOCOMOTIVE MICRO-IMPLANT USING ACTIVE ELECTROMAGNETIC PROPULSION

CROSS-REFERENCE TO RELATED APPLICATIONS

The application is a continuation of U.S. patent application Ser. No. 13/591,188 filed on Aug. 21, 2012, entitled "Method of Making and Using an Apparatus for a Locomotive Micro-Implant Using Active Electromagnetic Propulsion" which claims priority to and is a continuation-in-part of U.S. application Ser. No. 12/485,654 filed Jun. 16, 2009, entitled "Method Of Making And Using An Apparatus For A Locomotive Micro-Implant Using Active Electromagnetic Propulsion," and is a continuation-in-part of U.S. application Ser. No. 12/485,641 filed Jun. 16, 2009, entitled "Wireless Power Transmission for Implantable Medical Devices," which applications are expressly fully incorporated by reference herein.

This invention was made with Government support under Contract Number HR0011-10-03-0002 awarded by the Defense Advanced Research Projects Agency. The Government has certain rights in this invention.

FIELD OF THE ART

The field of the art relate to methods of making and using an apparatus for a locomotive micro-implant using active electromagnetic propulsion.

BACKGROUND

Locomotive implantable devices have numerous applications including sensing, imaging, minimally invasive surgery, and research. Many techniques have been used to generate motion, including mechanical solutions and passive magnetic solutions. Power sources dominate the size of existing active implant technologies, and this size constraint (typically in the cm-range) limits the potential for propulsion. Additionally, mechanical propulsion is inherently inefficient at the scale of interest.

Passive locomotion schemes have circumvented the power and efficiency issues, but require large field gradients and usually cannot generate vertical motion. In a passive magnetic propulsion technique, a force is exerted on a small ferromagnetic material with magnetic field gradients. The passive propulsion method typically employs MRI-like systems because the gradient fields must be large and precisely controlled. The gradient must be in the direction of movement, and even MRI systems cannot overcome the force of gravity for devices smaller than roughly 1 mm. The force scales poorly as the size is reduced because it is proportional to the volume of the object. From a practical perspective, generating large field gradients is complicated, and current technology is inadequate.

In addition to the passive method, it is also possible to use mechanical propulsion with active power. Mechanical propulsion is accomplished with a wide variety of techniques. A few possible methods include flagella/motors, pumps, and acoustic streaming. These designs typically suffer from low conversion efficiency from input power to thrust, especially as the Reynolds number decreases. There are losses associated with the conversion from electrical power to mechanical motion, and more loss associated with the conversion from mechanical motion to forward thrust. As a result of the low efficiency, a fairly substantial amount of power is required, and the power source dominates the size making it difficult to miniaturize.

SUMMARY

The embodiments described herein relate to methods of making and using an apparatus for a locomotive micro-implant using active electromagnetic propulsion.

In one embodiment magnetohydrodynamics (MHD) is used to generate thrust. In another embodiment, asymmetric drag forces (ADF) are used to generate thrust.

In the MHD embodiment is provided for usage within a predetermined magnetic field and a fluid comprising: a body; a source of power disposed on or within the body; at least three fluid electrodes disposed on the body, the at least three fluid electrodes providing for a plurality of current paths within the fluid between different ones of the at least three fluid electrodes, in the presence of the predetermined magnetic field, thereby causing a force that moves the locomotive implant; and a controller disposed on or within the body and adapted to receive directional control signals and to control the plurality of current paths within the fluid using the directional control signals.

In the ADF embodiment is provided for usage within a predetermined magnetic field comprising: a body having a shape that will experience asymmetric drag forces when rotating; a source of power disposed on or within the body; at least one current loop that receives an alternating current, the alternating current causing, in the presence of the predetermined magnetic field, a force that moves the locomotive implant; and a controller disposed on or within the body and adapted to receive directional control signals and to control the alternating current in the at least one current loop using the directional control signals.

Devices that use a combination of the MHD and ADF are also described.

Methods of using the above are also described.

BRIEF DESCRIPTION OF THE DRAWINGS

These and other aspects and features will become apparent to those of ordinary skill in the art upon review of the following description of specific embodiments in conjunction with the accompanying figures, wherein.

DETAILED DESCRIPTION OF THE PREFERRED EMBODIMENTS

Described herein is an improved locomotive implant device, and related method, for controlling the same, which can enhance functionality for a variety of applications, as well as provide new applications, as described herein. The locomotive implant as described hereinafter can be remotely powered, remotely controlled, capable of sending and receiving data, and is highly adaptable. As this application describes improvements to that described in the previously filed U.S. application Ser. No. 12/485,654 filed Jun. 16, 2009 entitled "Method Of Making And Using An Apparatus For A Locomotive Micro-Implant Using Active Electromagnetic Propulsion", it is intended that teachings and embodiments described in that application are usable with the teaching and embodiments described herein, and will be apparent to one of ordinary skill.

I. Overview

Figure 1:
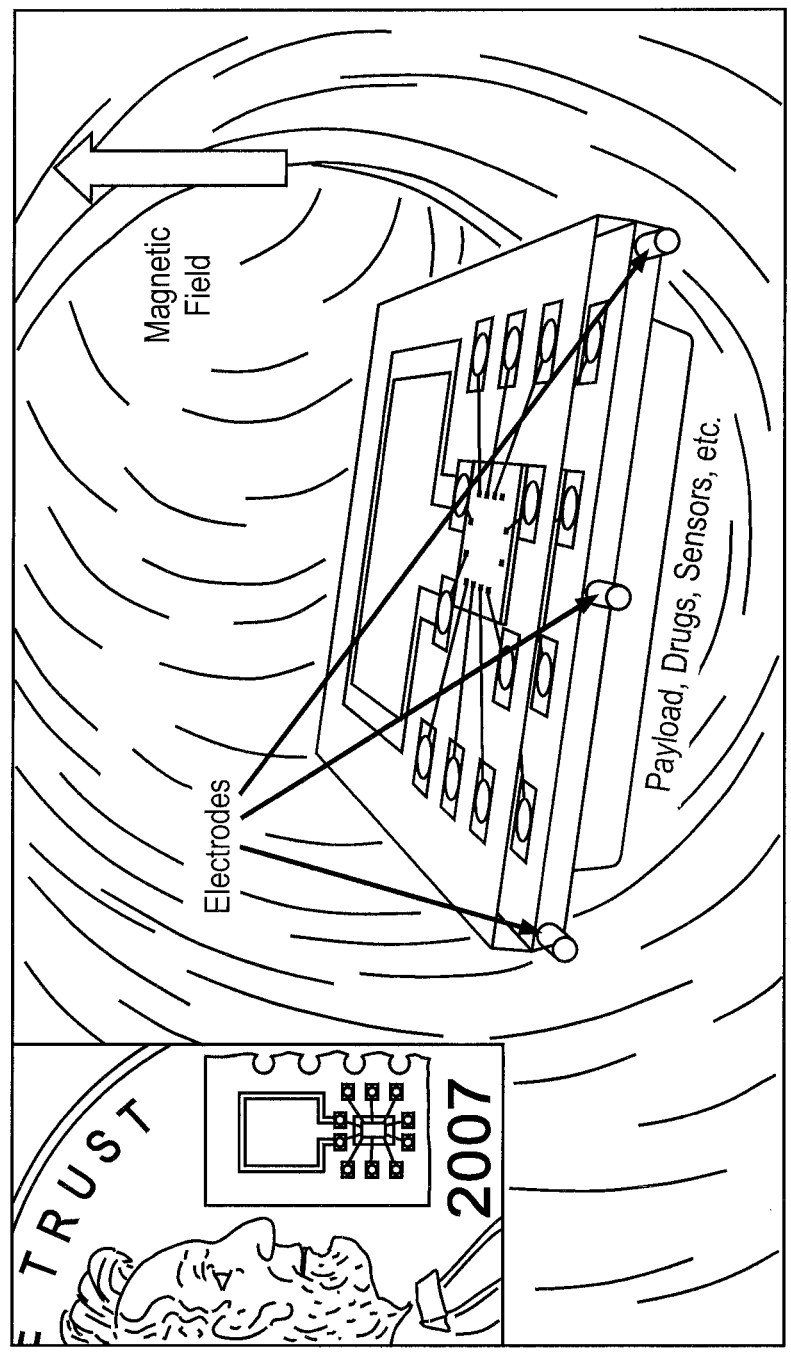
FIG. 1 illustrates a conceptual model of the FIG. 2(b) embodiment.

FIG. 1 shows the conceptual operation of one embodiment of an implant device travelling through the bloodstream with MHD propulsion. The implant device is comprised of a 2 mm×2 mm receive antenna and an integrated circuit that includes a matching network, a rectifier, a regulator, a demodulator, a digital controller, and high-current drivers that interface with the propulsion system. This implant device can travel through any fluid and can be navigated through the circulatory system, enabling a variety of new medical procedures. MHD propulsion can be directly steered by adjusting current flows into and out of electrodes to turn. 3D motion can be achieved by reorienting the external magnetic field, adjusting the buoyancy of the device, or by tilting the device and to create ascend or descend as the device moves. AFD propulsion can be steered by controlling and adjusting the total rotation as the device oscillates. For 3D motion, the magnetic field can be reoriented, the buoyancy can be adjusted, or it can be tilted up or down as it moves to ascend or descend.

The organization of the following descriptions is as follows. Section II presents the analysis and simulation of the fluid propulsion methods based on Lorentz forces. Section III describes the design of the wireless power transmission system as well as the data receiving architecture. The circuit implementation is presented in section IV, section V discusses the experimental results and summarizes performance, and Section VI provides other considerations.

II. Electromagnetic Propulsion

Propulsion for implantable devices has not been possible because of the high power requirement for mechanical designs, and the high complexity of passive magnetic designs. Our prior work based on Lorentz forces demonstrates two methods with significant advantages over existing techniques in terms of power efficiency, scalability, and controllability. The first method drives current directly through the fluid using magnetohydrodynamics (MHD), and the second switches current in a loop of wire to oscillate the device, which experiences asymmetric drag fluid forces. In both methods, the force is proportional to current, and therefore maximizing current will maximize the speed.

The thrust forces work against fluid drag forces, which are velocity dependent. This dependence varies with the Reynolds number of the fluid flow. The Reynolds number is a dimensionless representation of the ratio of the inertial forces to the viscous forces, and is given by $$Re = \frac{\rho_f vD}{\mu}$$

where $\rho_f$ is the density of the fluid, $v$ is the velocity, $D$ is a characteristic dimension, and $\mu$ is the fluid viscosity. For high Reynolds numbers (>1000), the drag force is given as $$D = \frac{1}{2}\rho_f v^2 A_f C_D \propto L^2$$

where $A_f$ is the frontal area of the device, and $C_D$ is the shape factor. These forces scale with area, and as will be shown, the thrust forces for both propulsion methods scale linearly with length. This means that in the high Reynolds regime, less current is needed to maintain a constant speed as the device is scaled. As the Reynolds number decreases, viscous forces become dominant. For extremely low Reynolds numbers (<1), the drag force scales linearly with the size of the device as predicted by Stokes Law. In the low Reynolds regime, the current must be kept constant as the device is scaled to maintain a constant speed. For mm-sized devices moving at cm/sec speeds in water, the Reynolds number ranges from roughly 10-100, so numerical fluid simulations are necessary for an accurate analysis of the fluid drag forces.

(a) Magnetohydrodyanmic (MHD) Propulsion

Figure 2C:
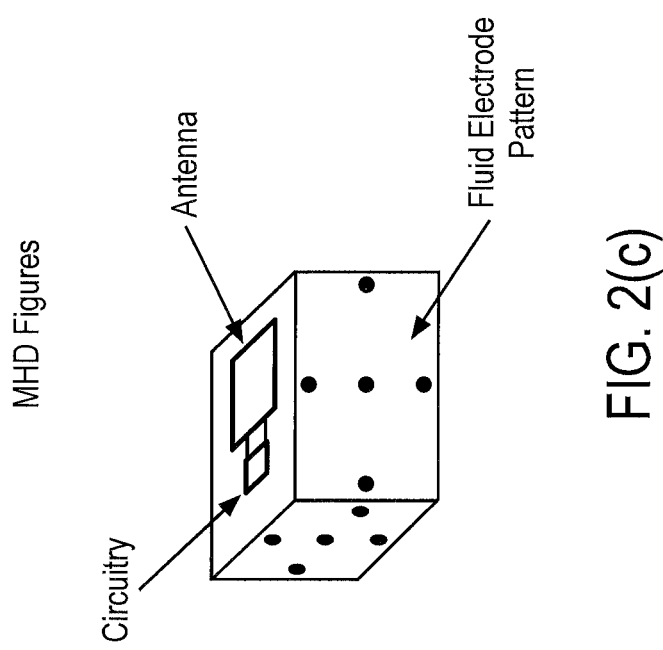
FIGS. 2(a-c) illustrate operation of the MHD propulsion embodiment and different embodiments of an MHD propulsion device.

MHD propulsion drives electric currents through fluids, so the efficiency of this method depends on the fluid conductivity. The basic principle of motion is described in FIG. 2(a-b), which illustrate thrust and steering according to one embodiment. Another MHD embodiment is illustrated in FIG. 2(c), and while it contains a different shape and additional fluid electrode patterns, with each electrode itself being independently controlled (and there could be many more electrodes in different positions if needed), the overall principles of motion remain the same, with there being extra degrees of control and therefore movement possible with the additional electrodes in different locations, as illustrated. It is also noted that shape is much less important than for the AFD embodiment also described herein, because the propulsion forces are generated directly. As such, the MHD device can be any desired shape, though preferably it should be designed to minimize drag and simplify control.

Considerations with respect to building an MHD device, in addition to those discussed further herein, include that the MHD device can be propelled with a static field and static currents. The MHD device requires, however, conductive fluids, as efficiency improves with conductivity. Further, the fluid electrodes must be carefully selected, as the fluid electrodes must not dissolve with current flow (platinum, for example). Electrolysis should also be minimized (Voltage/current adjustments, charge balancing).

The conductivity of human blood varies approximately from 0.2 S/m to 1.5 S/m depending on the concentration of blood cells. This translates to a load of less than 300Ω at the device, which varies with the size, shape, and distance between the electrodes as well as the temperature and applied voltage. Stomach acids tend to have higher conductivities but also vary significantly with normal biological processes. In the following analysis, the required current for a given speed will be estimated as a function of the size of the device and the background magnetic field. This will give insight into the scalability of the propulsion method and also provide a design target for the circuitry.

The thrust force for MHD propulsion is the Lorentz force on the current flowing through the fluid. These forces are given in the equation below, where I is the current in the wire, L is a vector representing the length and direction of the wire, and B is the background vector magnetic field:

$$F = IL \times B.$$

Figure 3:
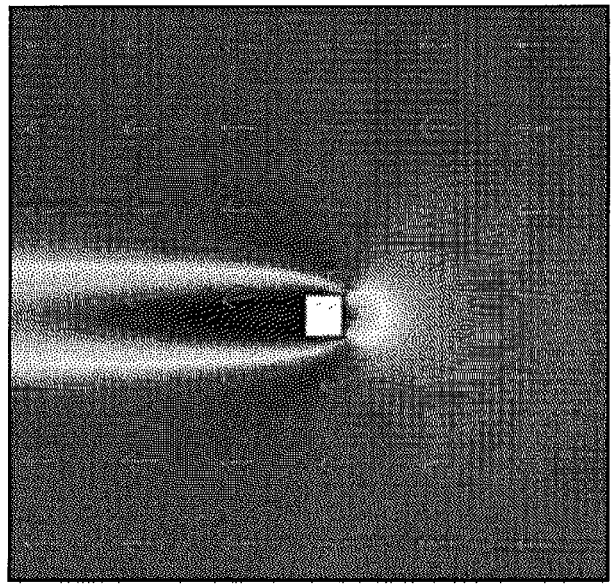
FIG. 3 illustrates simulated performance of the MHD propulsion embodiment.
Figure 3:
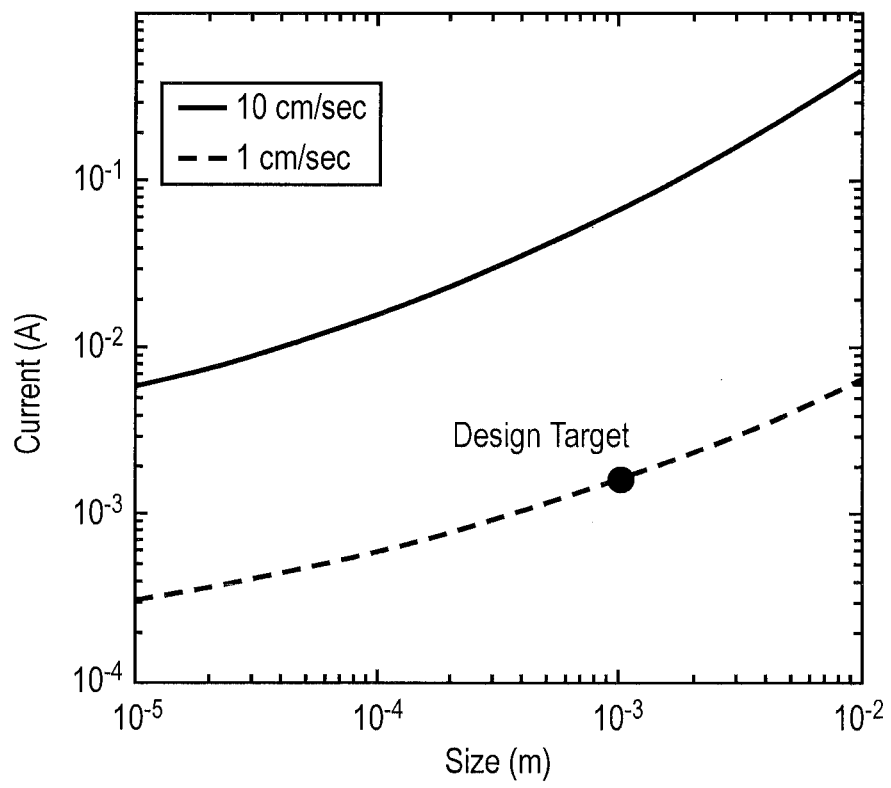

These forces scale linearly with the length of the wire L, which allows for the operation of very small devices. It scales more slowly than high Reynolds drag forces, which means that for smaller devices constant current scaling results in higher speeds; and it scales evenly with low Reynolds drag forces, which means that constant current scaling results in a constant speed. Additionally, the amount of force is linearly proportional to the background magnetic field, so the performance of this method improves with stronger magnetic fields. To accurately estimate the speed, numerical simulations of the fluid mechanics are performed. Fluid simulations based on incompressible Navier-Stokes flows predict the fluid drag forces, and from these forces the steady-state velocity can be extracted. In, FIG. 3, the required current is estimated for a given speed as a function of the size of the device with a background magnetic field of 0.1 T, which can be generated with permanent magnets. This analysis shows that mm-sized devices should be able to achieve speeds on the order of cm/sec with approximately 1 mA of current.

The amount of current that can be driven is a strong function of the fluid conductivity, and has significant non-linear variations with electrode area, electrode materials, applied voltage, and the types of ions in the fluid. To drive 1 mA through blood (which has the lowest conductivity of the targeted fluids), roughly 300 mV is required, resulting in a power consumption of around 300 μW. As the fluid conductivity increases, the required power decreases. These power requirements are within the bounds of optimized wireless powering techniques through tissue, so miniaturized locomotive implantable devices are possible with this method.

(b) Asymmetric Fluid Drag Propulsion

Figure 4A:
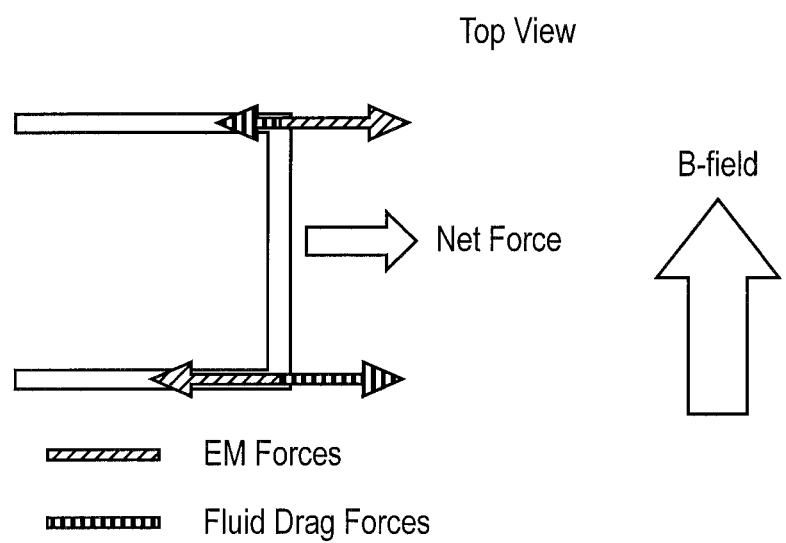
FIGS. 4(a-c) illustrate operation of the AFD propulsion embodiment and different embodiments of an AFD propulsion device.

The second fluid propulsion method relies on asymmetries in fluid drag created by an oscillating asymmetric structure. The structure is oscillated by alternating currents in a loop of wire that is placed in a background magnetic field. The basic principle of operation is described in FIGS. 4(a-b), which illustrate thrust and steering according to one embodiment. Another AFD embodiment is illustrated in FIG. 4(c), to illustrate another shape that experiences asymmetric drag forces. It should be apparent that a myriad of other shapes that would also experience asymmetric drag forces are possible, though, for example a cube won't work because each side will experience the same force as it rotates. Further while FIGS. 4(a-b) illustrate only one set of loops that are in the same orientation, in general, a single device could have 3 loops oriented orthogonally, which would allow the device to be tilted or rotated for better steering and motion control. Essentially, more loops give more degrees of control.

Considerations with respect to an AFD device include optimizing shape for maximum difference in drag. Also, the AFD device can operate in any fluid, as efficiency is determined by viscosity, rotation frequency, and angle of rotation. Further, feedback control can greatly enhance motion of the AFD device, which can be accomplished with sensors on device or external imaging.

The forces generated with this method are a function of the fluid viscosity, which for most bodily fluids are on the same order of magnitude as water. The performance of this method is enhanced as the number of loops is increased, and the amount of current that can be driven is limited by the internal resistance of the circuitry and the amount of power delivered through the antenna. The following analysis estimates the required current as a function of the size of the device and the desired speed. This analysis predicts the device scalability and also specifies the requirements on the circuitry.

The thrust forces result from asymmetric fluid drag on a structure that oscillates with electromagnetic torque of $$\tau_{em} = IL^2 B$$

where I is the current on the loop, L is the length of the wire, and B is the background magnetic field. The asymmetry in the fluid drag is represented by the shape factor, $C_D$. By integrating the fluid drag along one side of the device, the net force can be represented as $$F \propto (C_{D,H} - C_{D,L}) L^4 \omega^2$$

where $C_{D,H}$ and $C_{D,L}$ represent the different shape factors due to the asymmetry, L is a side length of device, and ω is the rotation frequency. Assuming small angle rotations and constant angular acceleration, which is true when the electromagnetic torque dominates the fluid drag torque, the average angular velocity over a half-cycle is $$\omega_{avg} = \sqrt{\theta \tau_{em}/(4I_{int})}$$

where θ is the angle of rotation and $I_{int}$ is the moment of inertia. Realizing that $\tau_{em} \propto L^2$ and $I_{int} \propto L^5$, constant current scaling results in the average angular velocity scaling as $\omega \propto L^{-3/2}$. Using this result in the equation for the net force, we again find that these thrust forces scale linearly with L. This method scales in the same way as MHD propulsion and allows for the operation of very small devices. As the Reynolds number decreases, the fluid drag becomes much more shape dependent, which complicates analytical analysis. For accurate estimations of the forces on these devices, we again rely on numerical simulations of the fluid mechanics.

Figure 5:
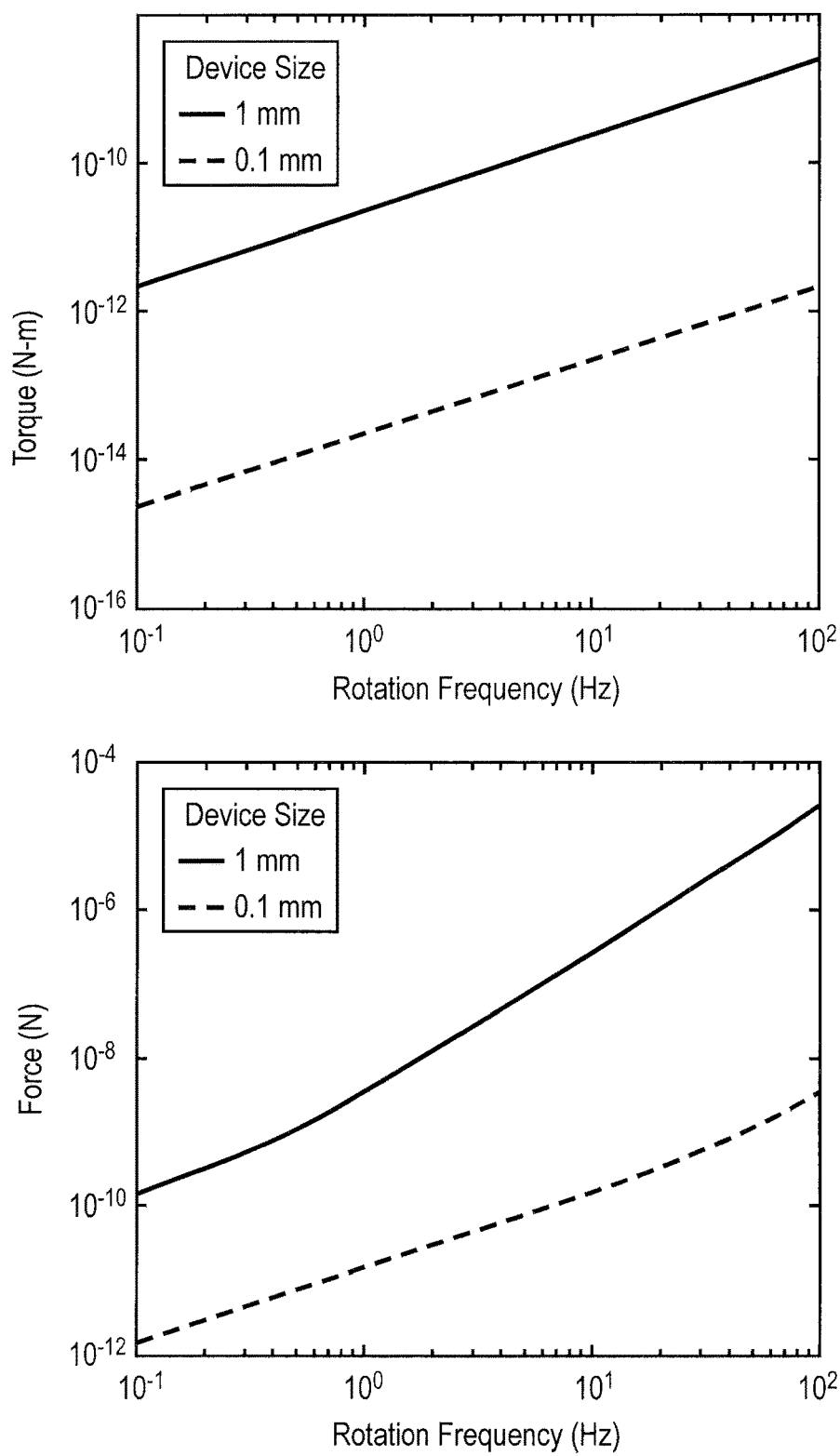
FIG. 5 illustrates simulations of drag torque and resulting net force for the AFD propulsion embodiment.
Figure 6:
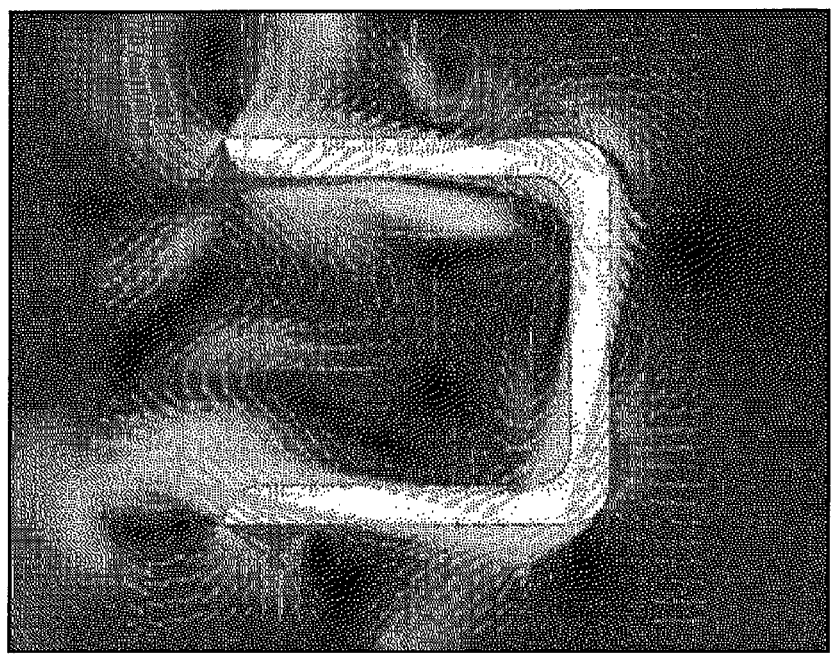
FIG. 6 illustrates simulated performance of the MHD propulsion embodiment
Figure 6:
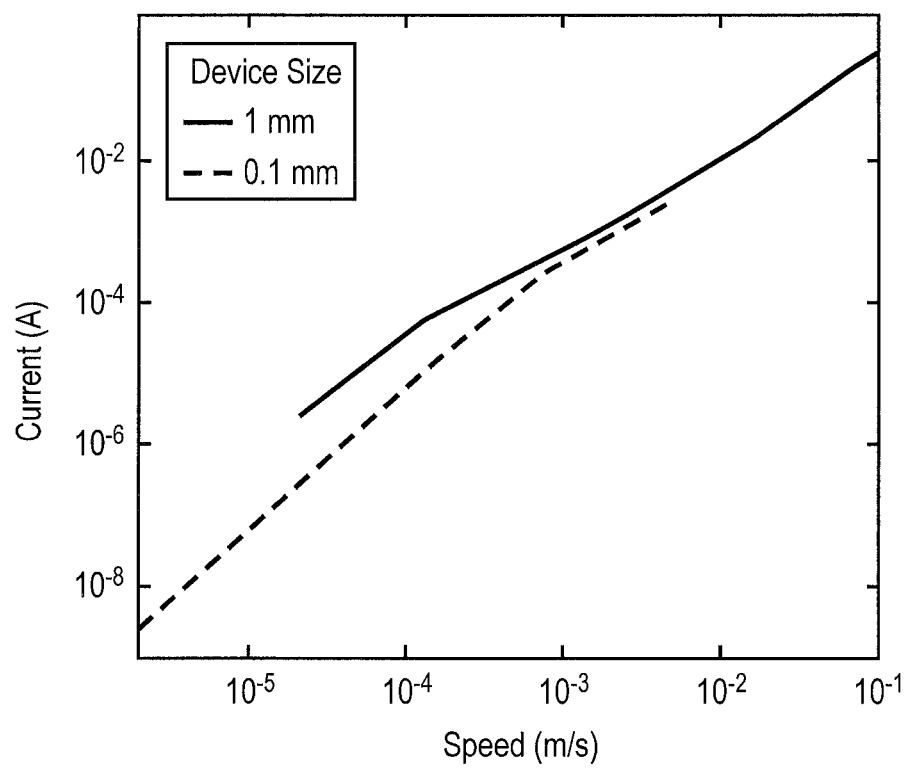

For this propulsion method, the simulations predict both the average fluid drag torque and the average net force over a cycle as a function of the rotation frequency and the size of the device. The fluid drag torque and the average force are shown in FIG. 5. These simulations agree with the predicted scaling behavior in terms of size and rotation frequency. From the fluid drag torque simulation, the current required to achieve a given rotation frequency can be estimated. The simulated net forces can then predict the speed, which relates to the current shown in FIG. 6. From these simulated results, mm-sized devices with a single loop of wire require currents of approximately 1 mA to achieve cm/sec speeds in water with a 0.1 T magnetic field. Additional loops of wire enhance the performance, essentially multiplying the current experiencing a force.

III. Wireless Chip Architecture

Figure 7:
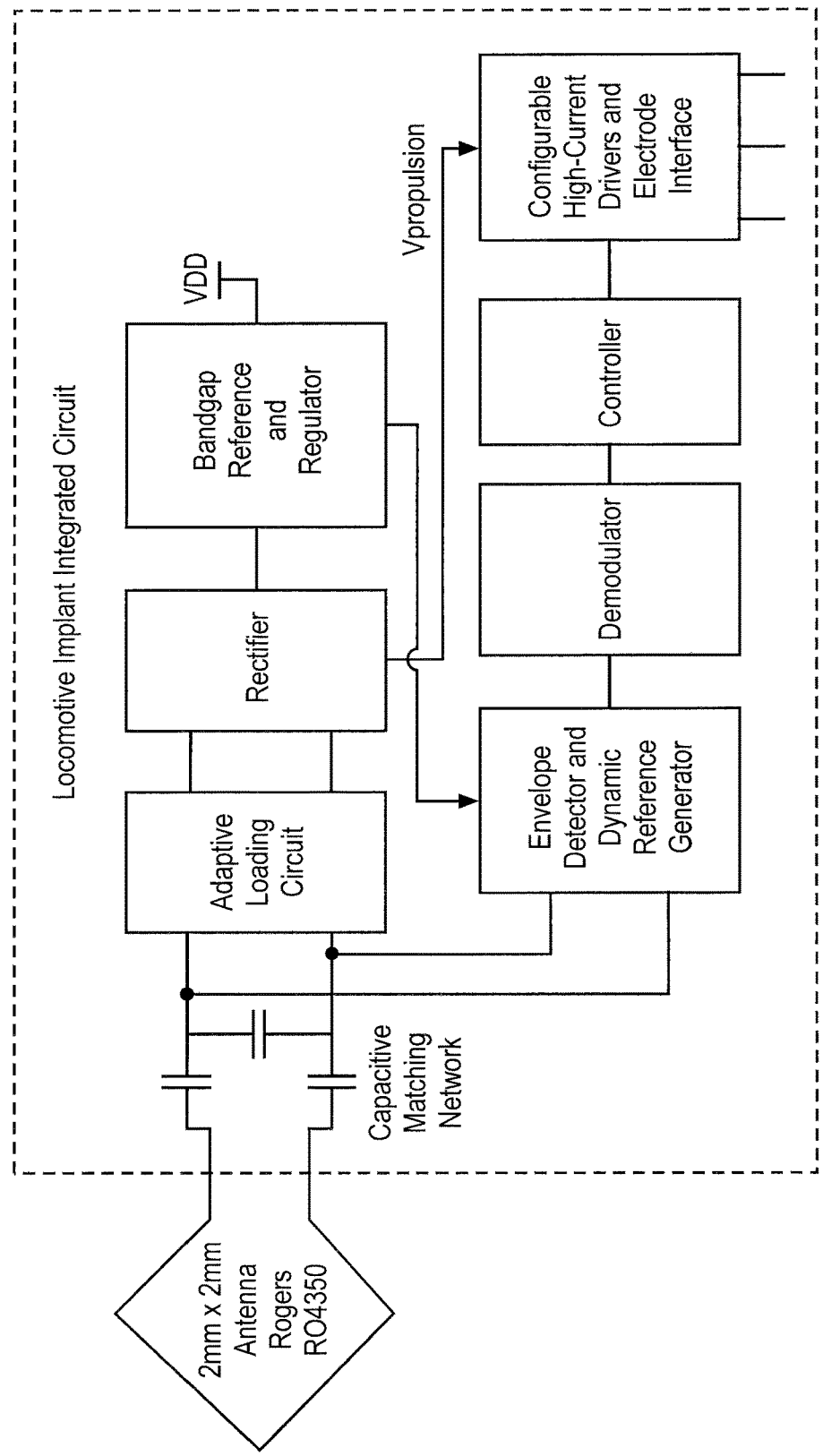
FIG. 7 illustrates an overview of an integrated circuit architecture for an embodiment.

The purpose of the chip was to create a wireless prototype that demonstrates the effectiveness of the propulsion system at the mm-scale. The specifications were derived from the requirements of the propulsion methods, which need approximately 1 mA of current for cm/sec speeds. The integrated circuit (IC) must receive both power and data from the external receiver to propel and navigate the device, and must operate with a limited power budget. The chip architecture is shown in FIG. 7, and the IC consists of a matching network, a charge-pump connected rectifier, a regulator, a bandgap reference circuit, a demodulator, a digital controller, and configurable electrode drivers. There are no external components except for the receiving antenna. The key challenge in this design is driving the high-current propulsion system efficiently and controllably while continuously harvesting RF energy. Power is the primary limitation, and minimizing power consumption was critical for the design.

The non-linear electrode-fluid resistance limits the minimum voltage required to drive the current, and is estimated at approximately 200-300 mV. The propulsion system dominates the power budget consuming over 90% of the total delivered power to the chip. The required 1 mA of current for propulsion needs to be sourced from no more than 300 mV while the active circuitry requires a regulated voltage of 700 mV and draws approximately 15 µA. Using a linear regulator for the propulsion system is inefficient, and a switching regulator requires large passive components, accurate on-chip clock, and complex controllers. Therefore, the chip was designed to drive the propulsion system from the first rectifier stage, which provides an unregulated 200-300 mV supply depending on the received power and can source the required current. Because the loading from the propulsion system varies with navigation, an adaptive loading network is also necessary to maintain effective matching at the antenna. The first rectifier stage is followed by three additional stages to boost the voltage, which is then regulated for the analog and digital circuits.

Figure 8:
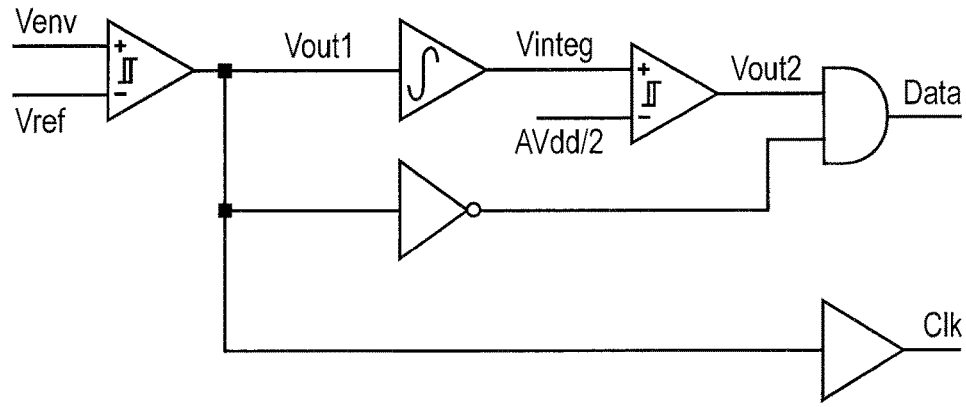
FIG. 8 illustrates the data receiver, including demodulator.
Figure 8:
Figure 8:
Figure 8:
Figure 8:
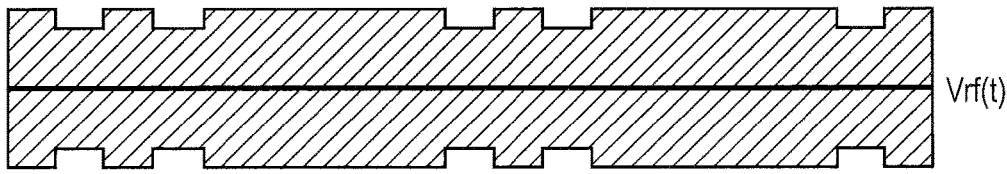
Figure 8:
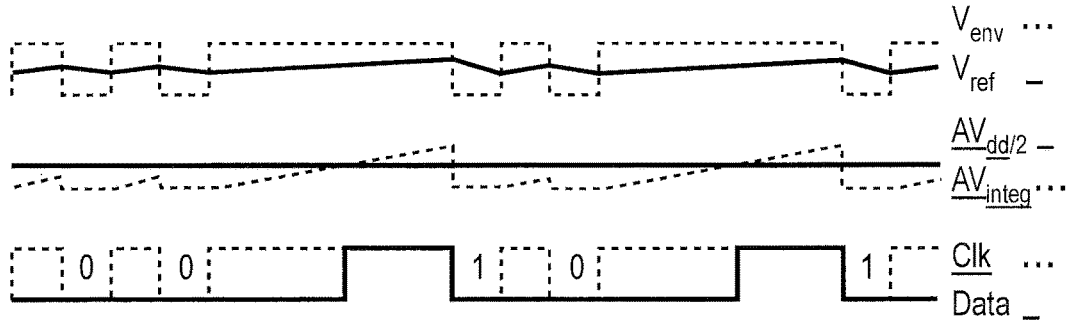

The size requirements prohibit the use of external energy storage components, so power must be continuously transmitted to the device. Power transmission must adhere to FDA safety regulations for tissue heating. From prior work, mm-sized antennas can receive approximately 200-300 µW at low-GHz frequencies safely. A 2 mm×2 mm antenna provides sufficient power for this design, and performing a frequency sweep with the antennas yields an optimal frequency of 1.86 GHz. It is important that the modulation scheme minimally affects the power transfer to the device because of the limited power budget. Frequency-shift keying (FSK) and phase-shift keying (PSK) operate with a constant envelope, but the demodulator requires either a frequency or phase-locked loop for carrier synchronization, which consumes significant power at high frequency. Amplitude modulation does not require carrier synchronization, and the modulation depth and duty cycle can be designed to minimize the impact on power delivery. For this reason, we implemented amplitude shift keying (ASK) with low modulation depth (minimum of 9%), and the pulse width (PW) encodes the data allowing for asynchronous clock and data recovery with simple circuitry. A high-level description of the data receiver is shown in FIG. 8. The demodulator provides both the clock signal for the digital controller and decodes incoming data. The demodulator interface with the matching network uses two rectifiers: the first has a small time constant and tracks the envelope, and the second has a large time constant and approximates the average of the envelope. These two signals are input to a comparator to generate the digital signal $V_{out1}$. This signal is buffered to produce a digital clock. $V_{out1}$ is also integrated and compared to a threshold to decode the data. With this implementation, long pulses produce high output and short pulses produce low output. The demodulated data is captured on the falling edge of the clock by a low-power digital controller, which configures the high-current electrodes for driving the propulsion system.

IV Circuit Implementation (a) Antenna and Matching Network

Figure 9:
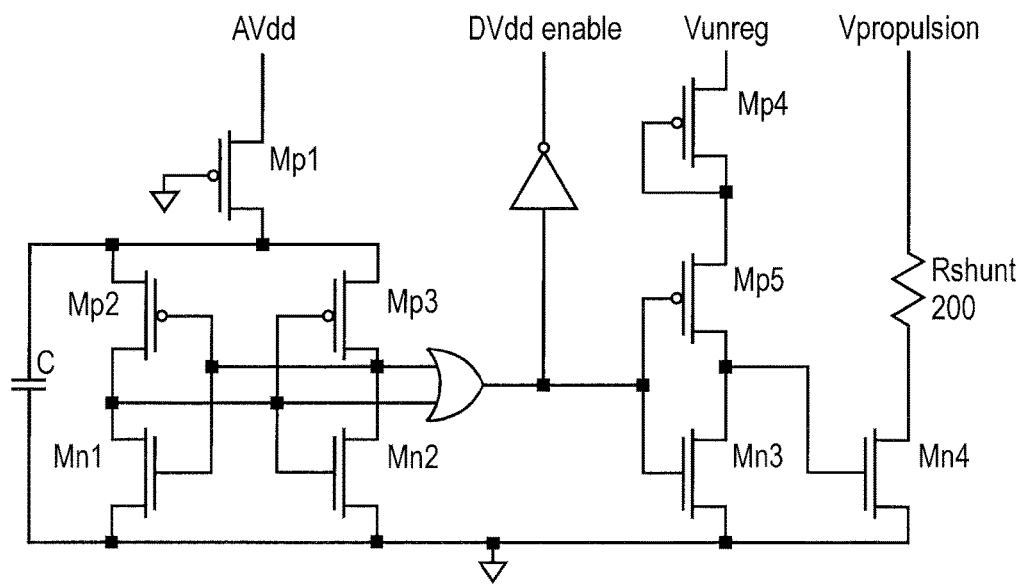
FIG. 9 illustrates power-on shunting and $V_{dd}$ enable circuit.

The antenna dominates the size of the prototype, and is implemented with a 2 mm×2 mm loop on a PCB using Rogers 4350 substrate. External components are not possible due to size constraints, so a balanced L-match consisting of only capacitors was implemented because on-chip inductors have significant loss and occupy large area. The total quality factor of the antenna and the matching network in air is estimated at 39. The chip input impedance is dominated by the propulsion system, and loading varies significantly during normal operation. Therefore, an adaptive loading network was implemented to maintain an effective match. When the chip is powered on and before the controller is reset, the gate of transistor $M_{n4}$ in FIG. 9 is weakly pulled up by $V_{unreg}$, which shunts the first rectifier stage with an internal 200Ω resistor. After the digital supply is enabled, the weak pull-down transistor $M_{n3}$ slowly turns off the shunt resistor. Once the power-on reset (POR) signal has been issued, the digital controller is reset and takes control of the network, adjusting the resistance based on incoming data.

(b) Start-Up and Power-On Reset Circuits

Figure 10:
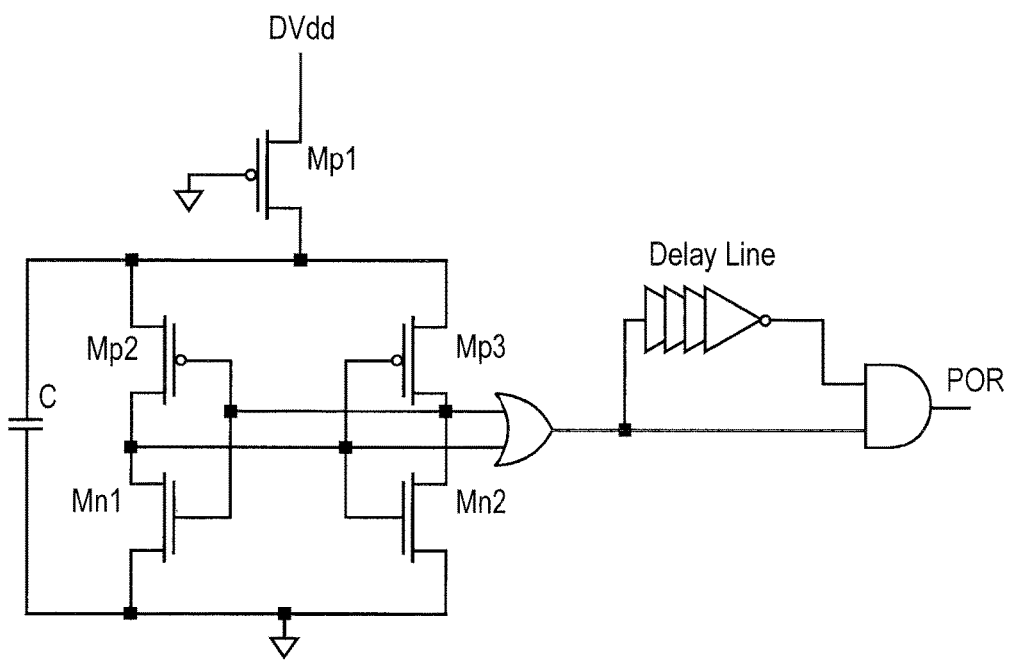
FIG. 10 illustrates power-on reset signal generation circuit.

Start-up circuitry for the initial power-on is necessary to ensure that the antenna impedance maintains a match and that the chip enters a known state. A start-up network that turns on a pass transistor for the digital supply voltage is shown in FIG. 9. The cross-coupled inverters are skewed in opposite directions to prevent metastability, and the delay is controlled by a capacitor at the supply of the cross-coupled inverters that slowly charges through a weak current source. This delay ensures that the analog supply voltage has reached a stable 700 mV before powering on the digital circuits. Once the digital supply is enabled, a POR pulse is issued after an additional delay. This pulse generation is shown in FIG. 10. The pulse width is set by the delay of a capacitively loaded inverter chain that provides a sufficient duration pulse to reset the controller.

(c) Power Management

When the antenna receives 500 µW, the RF input voltage to the rectifier is 350 mV. Conventional diode-capacitor ladder rectifiers suffer from low efficiency at low input voltage. Therefore, charge-pump connected self-driven synchronous rectifiers (SDSR) are used with low-Vt devices. The first stage of the rectifier is sized 10 times larger than the consecutive stages because the propulsion system is driven directly from this first stage. It outputs an unregulated 200-300 mV and drives roughly 1 mA of current. The remaining three stages are all sized the same and output 0.9-1.2 V while driving 15 μA. The pump capacitance between these three stages is 5 pF. The simulated efficiency of the rectifier is approximately 55%.

Figure 11:
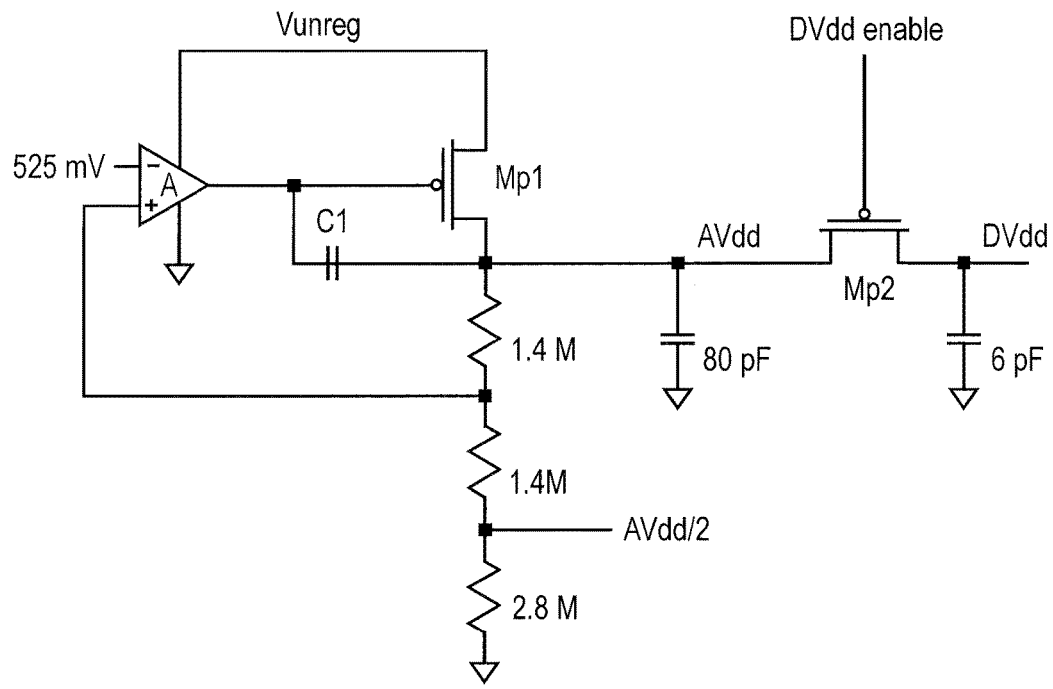
FIG. 11 illustrates the regulator circuit with both analog and digital supply.

The unregulated supply voltage fluctuates significantly with variations in available power due to varying link gain as the device moves, propulsion driver strength, and switching noise from the digital circuits. The device must also be insensitive to temperature variations. To create a stable 700 mV supply for the active circuitry, we implemented a low drop-out voltage regulator that relies on a bandgap reference circuit. A total of 86 pF of smoothing capacitance was used to maintain stable voltage at the supply. The schematic of the regulator is shown in FIG. 11. The regulated voltage is sampled via a resistive voltage divider and is compared to the bandgap reference output voltage of 525 mV. The resistive divider also outputs a voltage of Vdd/2, providing a reference for the demodulator. Capacitor C1 is added to help stabilize the feedback loop. The regulator has an overall efficiency of 58%. However, the dissipated power due to the rectifier inefficiency is only $$\eta_{degradation} = \frac{P_{lost}}{P_{total}} = \frac{(V_{unreg} - V_{reg}) * I_{reg}}{P_{propulsion} + P_{circuits}} = 3\%$$

of the total power consumption because the unregulated propulsion system dominates power usage.

(d) Clock and Data Recovery

Figure 12:
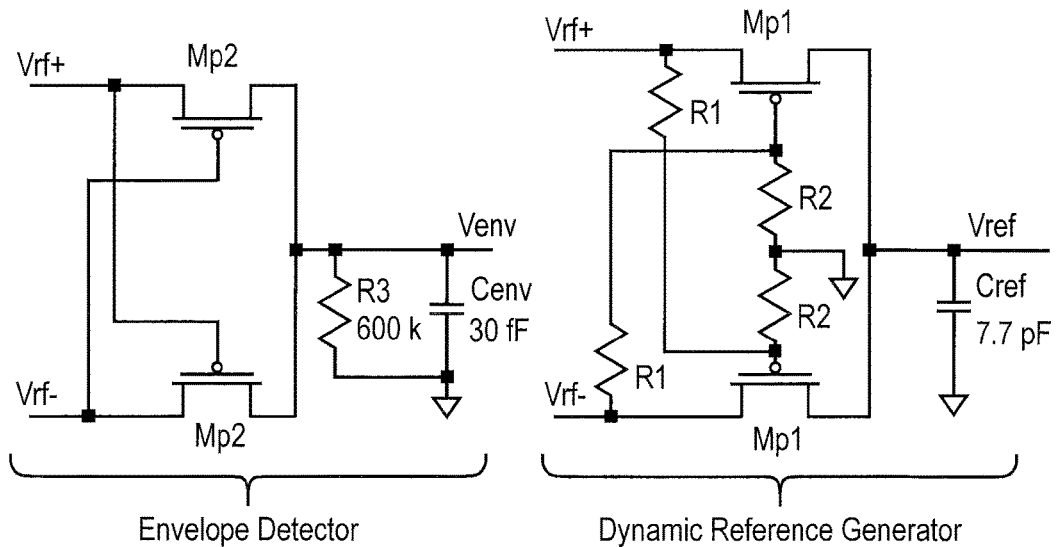
FIG. 12 illustrates envelope detection and dynamic reference voltage generation circuits.

The low modulation depth and fluctuating input power make it impossible to use a fixed reference voltage for the ASK threshold detector. Instead, a dynamic reference voltage is generated concurrently with envelope detection. The schematic of the envelope detector and dynamic reference generator is shown in FIG. 12. Both circuits use cross-coupled PMOS transistors to achieve full-wave rectification. The envelope detector RC time constant filters out the carrier and passes the data. In the dynamic reference generator, the RF input voltage is resistively divided to weakly turn on the cross-coupled transistors. The higher on-resistance and larger load capacitance form a large RC time constant, which effectively averages the envelope. The resistor at the output of envelope detector aligns the average of the envelope with the dynamically generated reference voltage.

Figure 13:
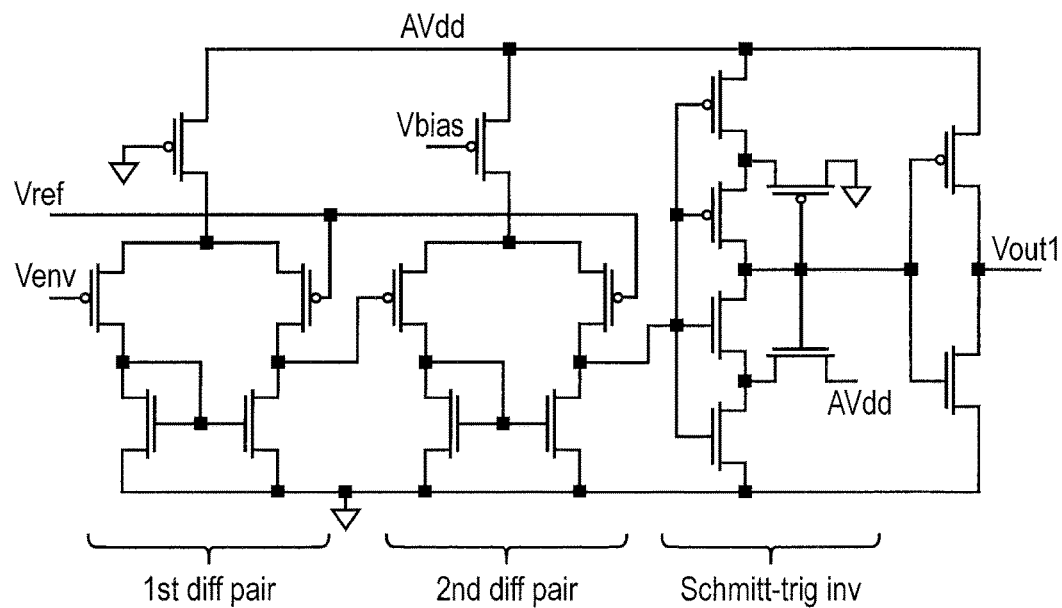
FIG. 13 illustrates a first comparator that converts the envelope into digital signal.
Figure 14:
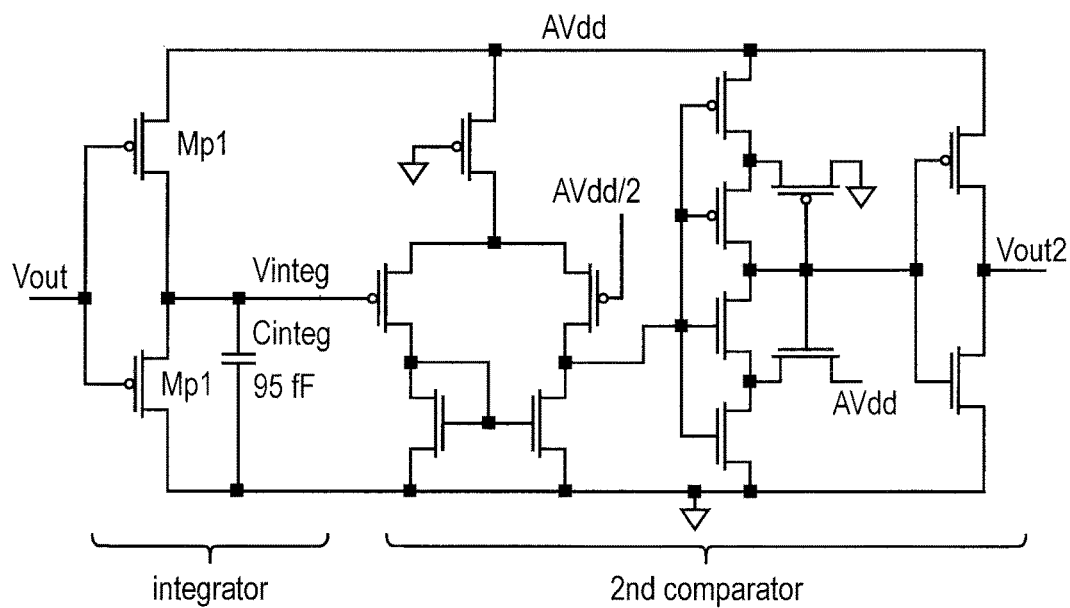
FIG. 14 illustrates an integrator and second comparator for data decoding.

Clock and data signals are recovered from the envelope and the dynamic reference, which are first input to a comparator to generate the full-swing digital signal $V_{out1}$. This comparator consists of two differential amplifier stages followed by a Schmitt-trigger inverter as shown in FIG. 13. Two low-power differential amplifiers ensure that the gain remains high for a wide range of common-mode input voltages, which vary depending on input power. The Schmitt-trigger inverter reduces the crowbar current due to slow transitions of the amplifier output, and it also decreases sensitivity to noise. The resulting digital signal is both buffered to generate the clock and integrated to decode the data as described in FIG. 14. The integrator consists of a skewed inverter with a capacitive load to provide slow rising and fast falling edges. This capacitance defines the pulse width that causes the data to transition from low to high, and therefore sets the minimum and maximum data rates. On the falling edge of each incoming pulse, data is captured from a comparator that compares the integrated result with a fixed reference at $V_{dd}/2$. This comparator consists of a single differential pair followed by a Schmitt-trigger inverter. The entire demodulation system draws a current of 5 μA.

(d) Controller

The digital controller receives data and clock signals from the demodulator, and configures the propulsion system drivers and the adaptive loading network. Data transmission begins with a 5-bit prefix that, when received, enables a shift register to begin accepting the 55-bit data packet. While data is being shifted into the register, the prefix detection circuitry is disabled. Once the entire packet is received, the shift register pushes all the data to a memory register that stores it until the next valid transmission. By only enabling the necessary circuitry in each stage of data reception, power consumption is minimized. Because the clock is derived from the data signal, when no data is being received the only current drawn is due to leakage. The estimated average power consumption of the digital controller while receiving data is 2 μW, and it occupies 0.009 mm².

(e) Configurable High-Current Drivers

The chip has 6 high-current electrode drivers with configurable strength to accommodate both propulsion mechanisms. Each of the drivers can be independently set to $V_{propulsion}$ from the first rectifier, ground, or left floating. Additionally, the driver strength can be controlled with 4 parallel transistors, and ranges from 20-1000Ω. This configurability is necessary to adapt to uncertainty in electrode-fluid resistance and to enable speed and steering control. Data in the memory register directly controls the electrode driver state and strength.

V Experimental Verification

Experimental tests verified all the elements of the design including wireless power transmission, the ASK-PWM data transfer, the analog and digital circuitry, and the two propulsion schemes. Independent tests evaluated the wireless link and the circuit performance, and testing of the complete system demonstrated navigation and propulsion through fluids. Each experiment will be described in detail in this section. The overall circuit performance is summarized in Wireless Power Transmission.

Figure 15:
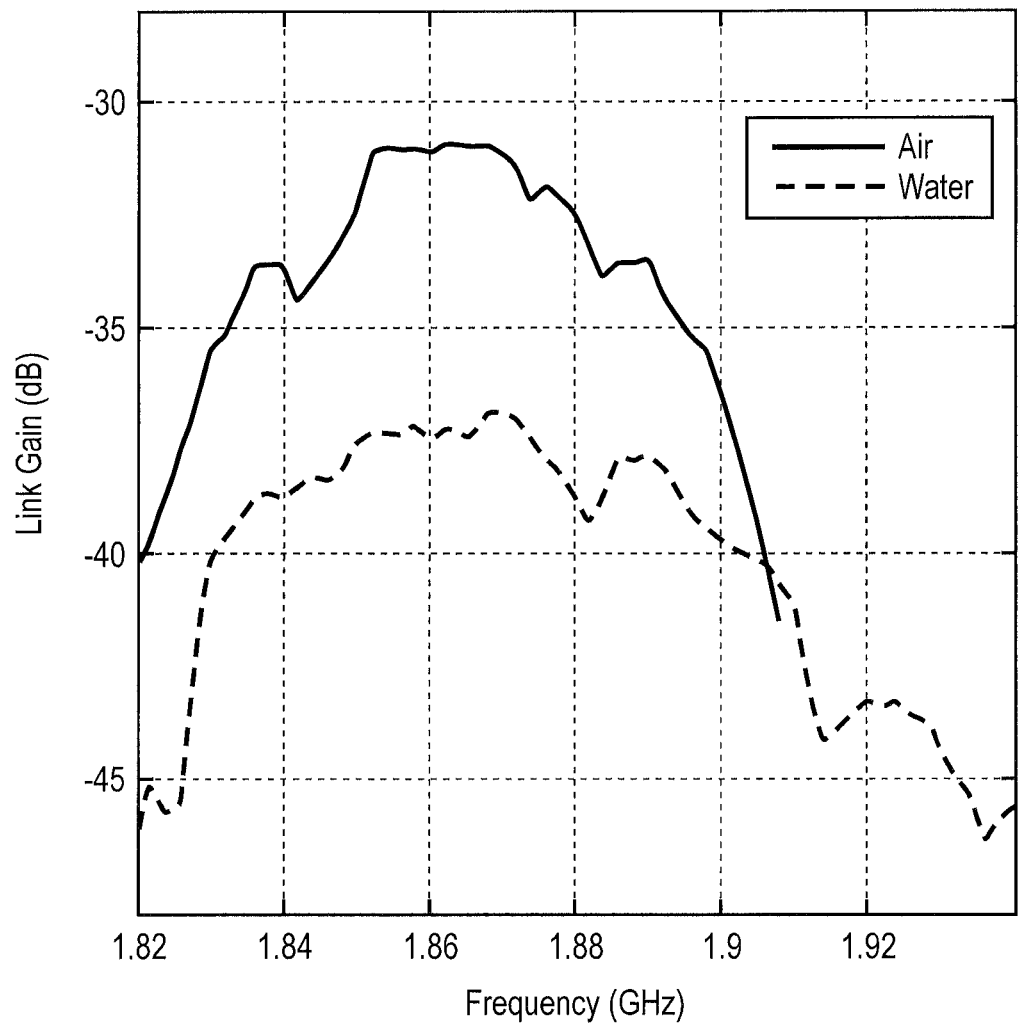
FIG. 15 illustrates measured link gain in air and water associated with the transmitter.
Figure 16:
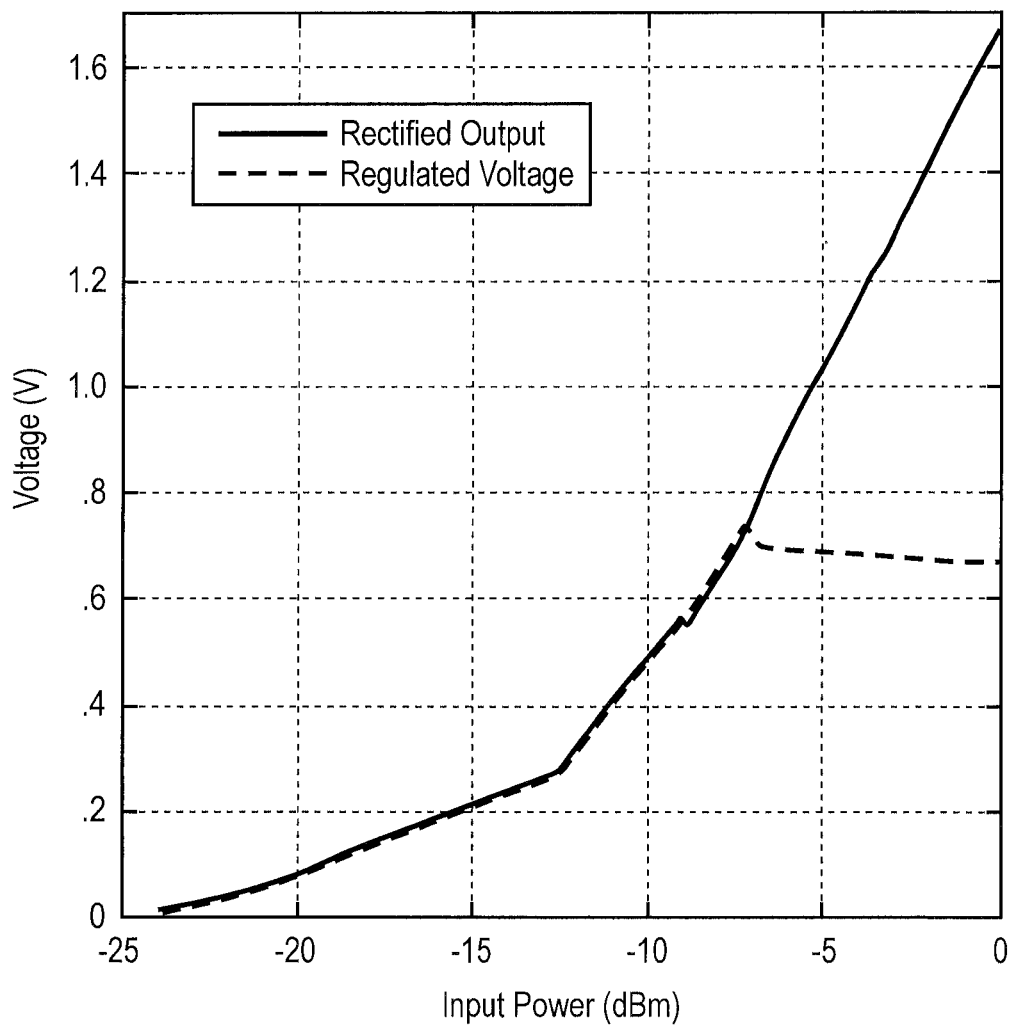
FIG. 16 illustrates plots of rectified output voltage and regulated voltage as a function of input power.

The transmitter consists of a signal generator, a high-frequency amplitude modulator, a power amplifier, and a 4 cm×4 cm loop antenna fabricated on PCB. The IC was wire bonded to a 2 mm×2 mm antenna fabricated on a Rogers 4350 substrate to minimize RF losses. A frequency sweep of the link gain was tested at a separation distance of 5 cm both in air and with the device placed on the surface of water. The measurements are shown in FIG. 15. From this plot, the quality factor in air is 39 for the antenna including the matching network. The rectified output voltage and the regulated voltage are plotted as a function of input power in FIG. 16, showing that the device first powers on with roughly −7 dBm. With a rectifier efficiency of approximately 55%, roughly 2 W must be transmitted to receive 500 μW, resulting in approximately 250 μW of usable power after rectification.

(a) ASK-PWM Data Transfer

Figure 17:
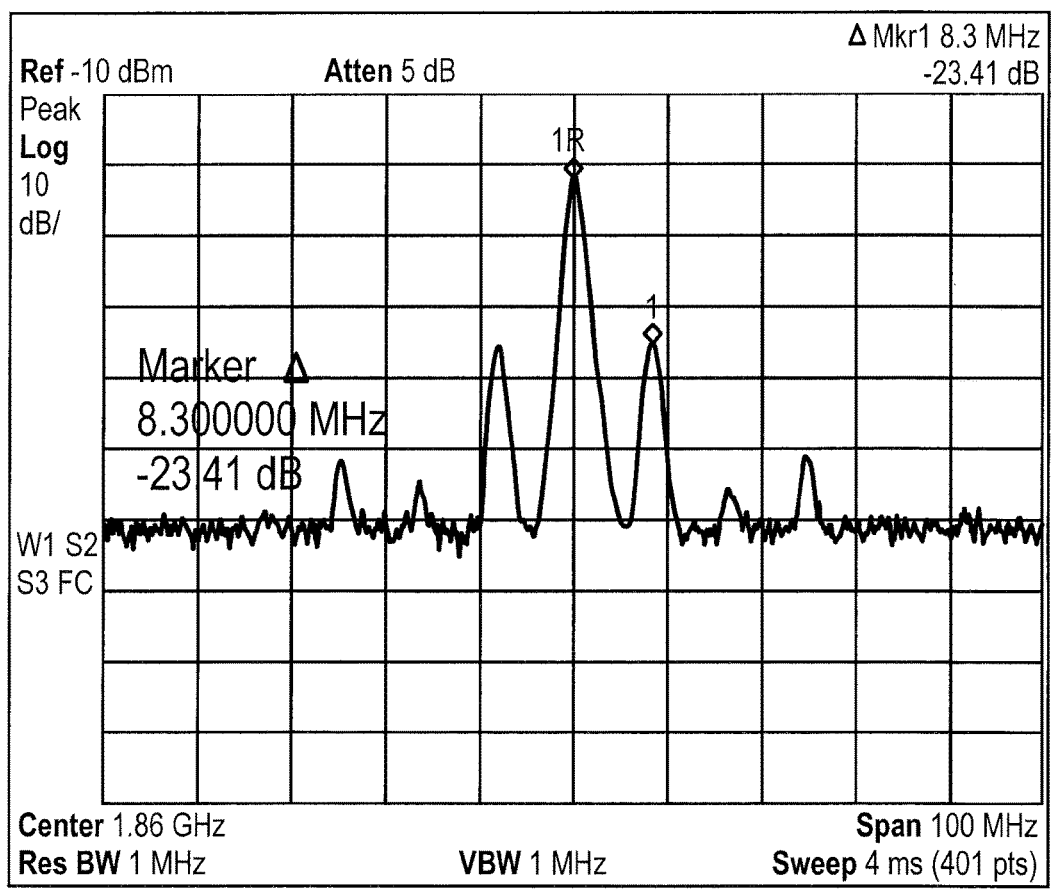
FIG. 17 illustrates the spectrum of the 1.86 GHz carrier modulated at 9% depth with an 8.3 MHz clock.
Figure 18:
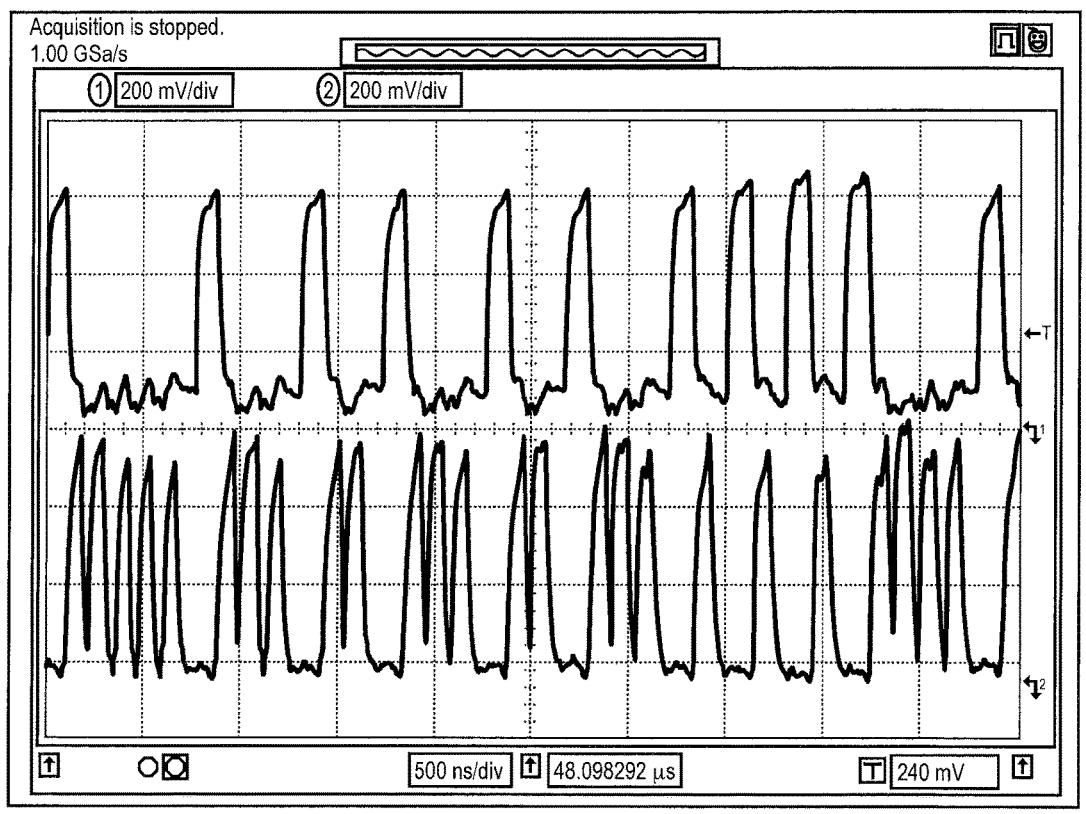
FIG. 18 illustrates measured waveforms of data and clock signal at the output of the demodulator.

Data modulation was designed to minimize impact on power delivery with a low power circuit implementation. To accomplish this, an asynchronous design was implemented that operates with minimal modulation depth and without carrier synchronization circuitry. This method allows for variable data rates and modulation depths. In order to test the range of operation, a versatile high-frequency modulator was constructed. The data signal was generated from an FPGA and input to the modulator, which modulates the output from the signal generator at an adjustable depth from 0-100%. The FPGA was able to stream data at up to 25 Mbps, and the chip properly received data from 2.5-25 Mbps. Additionally, the chip functioned with as low as 9% modulation depth. The spectrum of the carrier modulated at 9% with an 8.3 MHz clock is shown in FIG. 17, and the received clock and data signals on chip are shown in FIG. 18. The power consumption of the demodulating circuitry is approximately 5 μW at 10 Mbps, resulting in energy efficiency of 0.5 pJ/bit.

(b) Fluid Propulsion

The IC was designed to function with either of the described fluid propulsion mechanisms. The chip and receive antenna are encapsulated in RF-transparent epoxy to protect them from the fluid. The leads from the electrodes are exposed to adapt the device for use with either of the fluid propulsion methods. For MHD propulsion, these leads are positioned to directly connect to a conductive fluid, and salt water was used for testing. For the method relying on asymmetric fluid drag forces, the electrodes are connected to loops of wire that oscillate the device. In both test cases, the device floats on the surface of the water with a neodymium magnet placed next to the fluid to provide a magnetic field. Even though testing was performed on floating devices, both propulsion methods can function when fully submerged.

Figure 19:
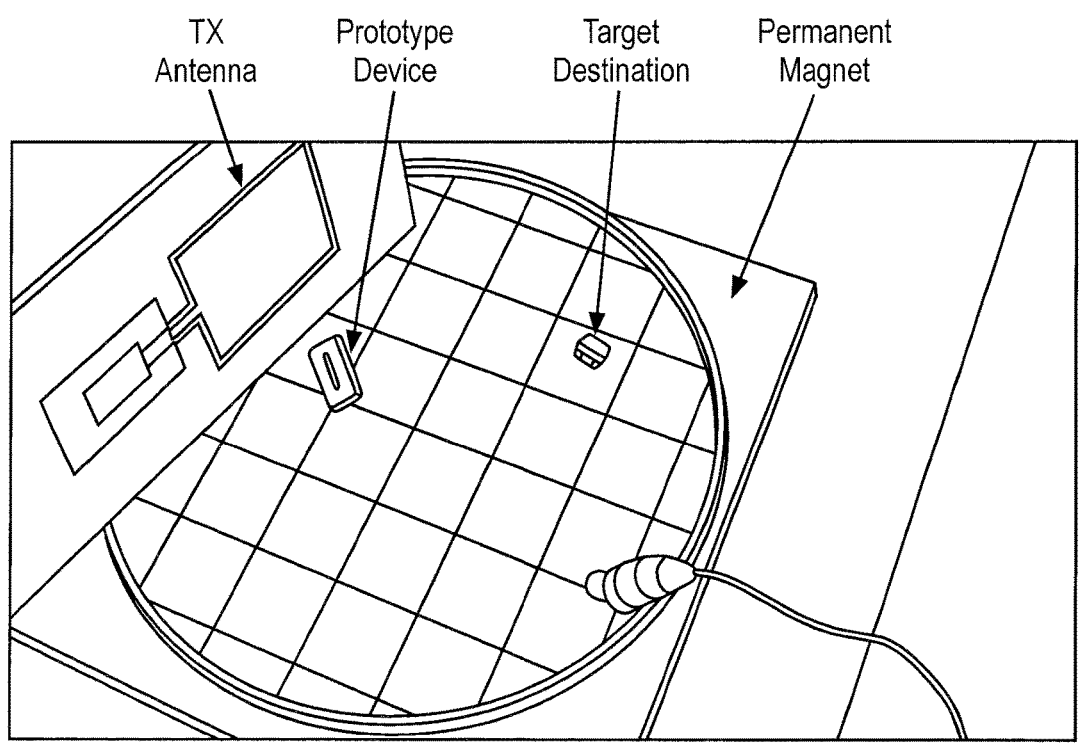
FIG. 19 illustrates a MHD propulsion set-up.
Figure 20:
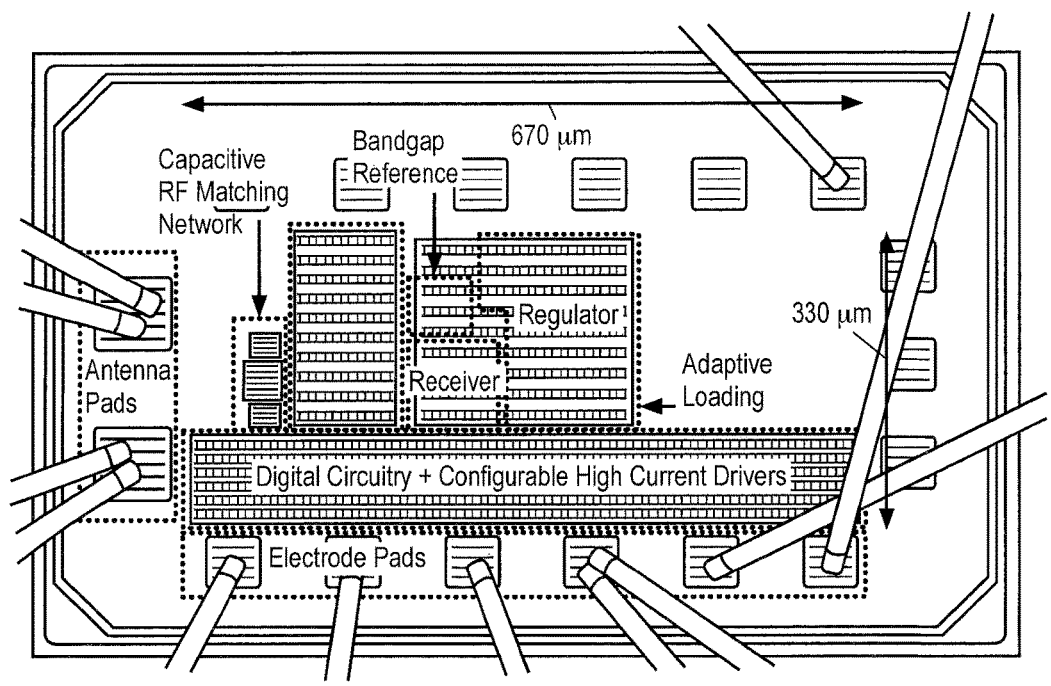
FIG. 20 illustrates an overview of the chip layout for the chip architecture illustrated in FIG. 7.

The experimental setup for MHD propulsion is shown in FIG. 19. During propulsion testing, the external antenna tracked the device at a distance ranging from 2 to 5 cm. Data is continuously transmitted with commands to control the motion. The device achieves speeds of up to 0.53 cm/sec in a 0.06 T field with approximately 1 mA, and can be navigated successfully along the surface of the water. Performance improves as the magnetic field is increased, so MRI systems will generate approximately 100 times as much propulsion force.

The setup for asymmetric fluid drag propulsion is very similar to MHD propulsion. The device is connected to 40 loops of wire, which are oriented to oscillate it. The prototype has an attached fin that experiences asymmetric fluid drag when oscillating. By changing the orientation of the magnetic field, the device can oscillate along the surface of the water, or into and out of the water. The external antenna is again placed above the device and continuously transmits data. The forces on the device are much stronger for this method because of the additional loops and smaller load; however propulsion is much more difficult to control. This method is also more sensitive to non-uniformities in the magnetic field. Additionally, the antenna link degrades as the device rotates, causing frequent errors in data reception. For this method to operate effectively, a new antenna link and a feedback controller are necessary.

TABLE I

| PERFORMANCE SUMMARY | |
| --- | --- |
| Rectifier | |
| Rectifier Topology | 1 + 3 Asynchronous Self-Driven |
| Load @ 0 dBm | 0.5-2 mA @ 0.2 V (unreg) |
| | 20 μA @ 0.7 V (reg) |
| Efficiency @ 0 dBm | 55% |
| Rectifier Chip Area | 0.3 mm² |

TABLE I-continued

| PERFORMANCE SUMMARY | |
| --- | --- |
| Bandgap Reference and Regulator | |
| Bandgap Power Consumption | 5 μW @ 1.2 V, 25° C. |
| Regulator Efficiency | 60% |
| PSRR | −20 dB (@8.5 MHz) |
| On-chip regulation capacitance | 72 pF |
| Bandgap Reference Chip Area | 0.0025 mm² |
| Regulator Chip Area | 0.03 mm² |
| Demodulator | |
| Modulation Type | ASK + PWM |
| Carrier frequency | 1.86 GHz |
| Data Rate | 2.5-25 Mbps |
| Power Consumption | 5 μW @ 10 Mbps |
| Sensitivity | −10 dBm |
| Modulation Depth | ≥9% |
| Energy per bit | 0.5 pJ/bit |
| Demodulator Chip Area | 0.007 mm² |
| Power Breakdown | |
| Bandgap Reference | 5 μW |
| Regulator | 5 μW |
| Demodulator | 5 μW |
| Digital Controller | 2 μW |
| Fluid Propulsion System | 250 μW* |
| Total | 267 μW |

*Varies with input power and loading from propulsion

VI. Other Considerations

Other considerations with respect to both the MHD and the AFD embodiments are that the magnetic field can be static or time varying, using permanent magnets, electromagnets, on device or external magnets, as well as current on the device to control motion.

3D control can be achieved by re-orienting the magnetic field to move in different directions, orthogonal loops of wire can also be used to tilt the device Adjusting the buoyancy will have an effect on 3D control. This can accomplished with mechanical deformation of the shape such as adjusting the size of an air pocket or the volume of the device itself. The density of the materials could also be adjusted by controlling the temperature. Additionally gases can be created from the fluid through the process of electrolysis for MHD, and these gases can adjust buoyancy.

Adjusting the buoyancy will have an effect on 3D control. This can be accomplished with mechanical deformation of the shape such as adjusting the size of an air pocket or the volume of the device itself. The density of the materials could also be adjusted by controlling the temperature. Additionally gases can be created from the fluid through the process of electrolysis for MHD, and these gases can adjust buoyancy.

Adjustment of the exterior shape of the body can accomplish different objectives, including having an effect on or adjusting buoyancy, minimizing drag, controlling drag, as well as creating lift forces or other steering forces.

The devices described herein can be used in numerous different environments, One class of environments relate to the body of an animal, including a human, such as most body cavities, digestive system, circulatory system, bladder, nasal cavity, ear canal, brain electrodes/devices. Another class of environments relates to industrial operations, such as pumps/compressors, water treatment, seawater, pipelines, etc.

Multiple different devices can also be used within the same environment. Each are independently controllable, provide for independent communication (being independently addressable), and can be fitted with sensors, actuators, active circuit elements, cameras, or cargo (such as drugs).

The material used to build the body will differ depending upon the environment in which it is used. For body environments, for example, biocompatible plastics/materials (such as PVC) for encapsulation, can be used. Non-magnetic materials are preferred because they do not interfere with the exterior magnetic field. Different materials can also be chosen based upon buoyancy characteristics.

The overall size of these devices can also be scaled for large and small applications, down to sub-mm sizes if needed.

Both locomotion methods could also be used to reposition specific elements attached to the main device independently, and such adjustments could apply to the antenna, sensors, actuators, active circuit elements, cameras, or cargo to improve their functionality without disturbing the position and orientation of the main device.

Further, single devices that each use both MHD and AFD for overall control and positioning of the device are within the intended scope of the present invention.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures. It is intended that the scope of the appended claims include such changes and modifications.

What is claimed is:

1. An apparatus for wireless power and data transfer to an implantable device operating in a biological environment, the apparatus comprising:
    a wireless power transmitter operating at a power signal frequency and having one or more transmitting antennae configured to transmit a power signal modulated with data over a radio frequency (RF) carrier signal; and
    a wireless power receiver having one or more receiving antennae configured to receive the transmitted power signal as a received power signal, wherein the wireless power receiver in integrated into the implantable device; wherein the implantable device further comprises:
        a rectifier, a regulator, a digital controller, and a charging device that accumulates energy over time, and
        a demodulator that decodes data modulated on the power signal without synchronizing to the RF carrier signal.

2. The apparatus according to claim 1, wherein the power signal frequency has a wavelength usable in the biological environment, and the wireless power transmitter and the wireless power receiver are spaced apart by a distance in the range between wavelength/100 and wavelength*100.

3. The apparatus according to claim 1, wherein the wireless power transmitter and the wireless power receiver include respective impedance tuning circuits that help maximize power transfer between the wireless power transmitter and wireless power receiver using simultaneous conjugate matching.

4. The apparatus according to claim 1, wherein the implantable device does not include a battery.

5. The apparatus according to claim 4, wherein the charging device includes a capacitor for storing energy.

6. The apparatus according to claim 5, wherein power is supplied continuously by the transmitted power signal.

7. The apparatus according to claim 1, wherein an adaptive loading network maintains effective matching for the one or more receiving antennae on the power receiver.

8. The apparatus according to claim 1, wherein the data is modulated with a low-depth amplitude modulation technique.

9. The apparatus according to claim 8, wherein a dynamic reference generator is included in the implantable device to recover an envelope from the low-depth amplitude modulation.

10. The apparatus according to claim 1, wherein the digital controller recovers clock and data information asynchronously.

11. The apparatus according to claim 10, wherein the asynchronous recovery occurs without a bit, symbol or other data rate clock embedded in the transmitted data.

12. The apparatus according to claim 1, wherein the one or more receiving antennae are smaller in area than the one or more transmitting antennae.

13. The apparatus according to claim 12, wherein the one or more receiving antennae are up to 100 times smaller in area than the one or more transmitting antennae.

14. The apparatus according to claim 1, wherein data is transferred from the implantable device to the wireless power transmitter by varying the impedance of the one or more receiving antennae.

15. The apparatus according to claim 1, wherein the rectifier, regulator, demodulator, and digital controller are implemented on a single integrated circuit.

16. The apparatus according to claim 1, wherein the wireless power transmitter communicates with a plurality of implantable devices operating in the same biological environment, each of the plurality of implantable devices being independently addressable and controllable.

17. An apparatus for wireless power transmission to an implantable device operating in a biological environment, the apparatus comprising:
    a wireless power transmitter operating at a power signal frequency and having one or more transmitting antennae configured to transmit a power signal over a carrier signal and a first match circuit with a tuned impedance; and
    a wireless power receiver having one or more receiving antennae configured to receive the transmitted power signal as a received power signal and a second match circuit with a tuned impedance, wherein the wireless power receiver in integrated into the implantable device; and
    wherein the implantable device further includes a rectifier and an adaptive loading network to compensate for varying load of the implantable device to maintain effective matching at the one or more receiving antennae.

18. The apparatus according to claim 17, wherein the power signal frequency has a wavelength usable in the biological environment and the wireless power transmitter, and the wireless power receiver are spaced apart by a distance in the range between wavelength/100 and wavelength*100.

19. The apparatus according to claim 17, wherein the first and second match circuits are tuned using simultaneous conjugate matching.

20. The apparatus according to claim 17, wherein the implantable medical device includes a controller that configures the adaptive loading network.

21. The apparatus according to claim 20, wherein the controller configures the adaptive loading network based on information transmitted from the wireless power transmitter.

22. The apparatus according to claim 17, wherein the transmitted power signal is modulated with data, which is received by the one or more receiving antennae.

23. The apparatus according to claim 22, wherein the data is transferred without synchronizing to a frequency of the carrier signal over which the power signal is transmitted.

24. The apparatus according to claim 17, wherein data is transferred from the implantable device to the wireless power transmitter by varying the impedance of the one or more receiving antennae.

* * * * *